(12) United States Patent
Limon et al.

(10) Patent No.: US 9,192,494 B2
(45) Date of Patent: Nov. 24, 2015

(54) LOCKING POLYMER STENTS

(75) Inventors: Timothy A. Limon, Cupertino, CA (US); David C. Gale, San Jose, CA (US); Bin Huang, Pleasanton, CA (US); Klaus Kleine, Los Gatos, CA (US)

(73) Assignee: Advanced Cardiovascular Systems, Inc., Santa Clara, CA (US)

( * ) Notice: Subject to any disclaimer, the term of this patent is extended or adjusted under 35 U.S.C. 154(b) by 0 days.

(21) Appl. No.: 12/709,418

(22) Filed: Feb. 19, 2010

(65) Prior Publication Data
US 2010/0256740 A1 Oct. 7, 2010

Related U.S. Application Data

(62) Division of application No. 11/215,713, filed on Aug. 29, 2005, now abandoned.

(51) Int. Cl.
*A61F 2/06* (2013.01)
*A61F 2/915* (2013.01)
*A61F 2/91* (2013.01)

(52) U.S. Cl.
CPC . *A61F 2/915* (2013.01); *A61F 2/91* (2013.01); *A61F 2002/91591* (2013.01); *A61F 2220/0008* (2013.01); *A61F 2230/0054* (2013.01)

(58) Field of Classification Search
CPC ... A61F 2/91; A61F 2/915; A61F 2002/9155; A61F 2002/91591; A61F 2220/0008; A61F 2230/0054
USPC ............................... 623/1.15, 1.16, 1.18, 1.2
See application file for complete search history.

(56) References Cited

U.S. PATENT DOCUMENTS

| | | | |
|---|---|---|---|
| 6,540,777 B2 * | 4/2003 | Stenzel | 623/1.16 |
| 6,562,067 B2 * | 5/2003 | Mathis | 623/1.16 |
| 2002/0107563 A1 * | 8/2002 | Shanley | 623/1.15 |
| 2003/0135266 A1 | 7/2003 | Chew et al. | |
| 2003/0199969 A1 | 10/2003 | Steinke et al. | |
| 2004/0093077 A1 * | 5/2004 | White et al. | 623/1.16 |
| 2005/0203607 A1 | 9/2005 | Scherrible | |

\* cited by examiner

*Primary Examiner* — Victor Nguyen
*Assistant Examiner* — Sarah Simpson
(74) *Attorney, Agent, or Firm* — Squire Patton Boggs (US) LLP

(57) ABSTRACT

Radially expandable implantable medical devices, such as stents, with locking elements are disclosed.

17 Claims, 11 Drawing Sheets

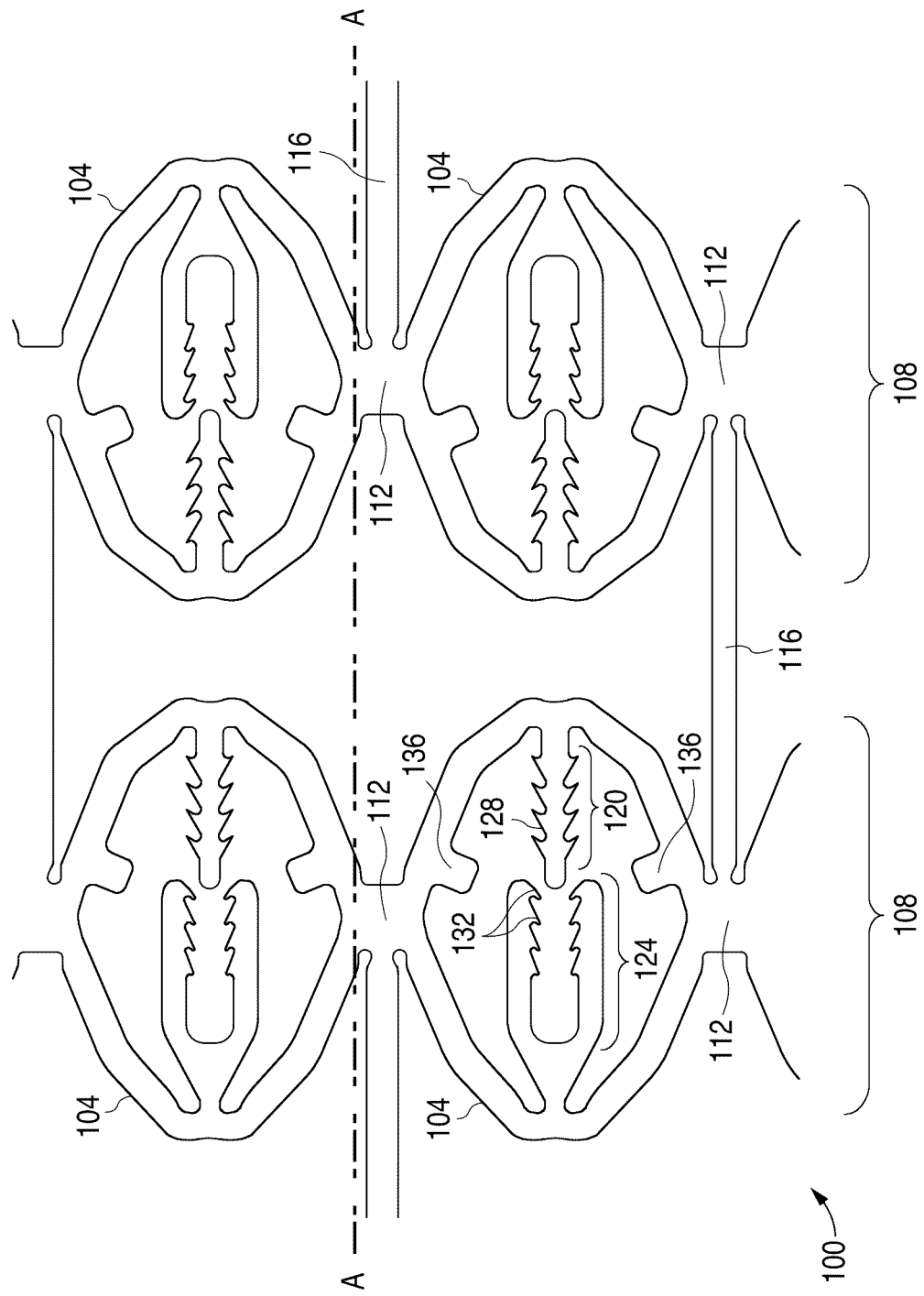

LOCKING POLYMER STENTS

CROSS-REFERENCE TO RELATED APPLICATIONS

This application is a divisional application of U.S. application Ser. No. 11/215,713, filed on Aug. 29, 2005, now abandoned and is hereby incorporated by reference in its entirety.

BACKGROUND OF THE INVENTION

1. Field of the Invention

This invention relates to radially expandable implantable medical devices such as stents for implantation into a bodily lumen. In particular, the invention relates to stents with locking mechanisms for locking a stent at an expanded radius.

2. Description of the State of the Art

This invention relates to radially expandable endoprostheses, which are adapted to be implanted in a bodily lumen. An "endoprosthesis" corresponds to an artificial device that is placed inside the body. A "lumen" refers to a cavity of a tubular organ such as a blood vessel.

A stent is an example of such an endoprosthesis. Stents are generally cylindrically shaped devices, which function to hold open and sometimes expand a segment of a blood vessel or other anatomical lumen such as urinary tracts and bile ducts. Stents are often used in the treatment of atherosclerotic stenosis in blood vessels. "Stenosis" refers to a narrowing or constriction of the diameter of a bodily passage or orifice. In such treatments, stents reinforce body vessels and prevent restenosis following angioplasty in the vascular system. "Restenosis" refers to the reoccurrence of stenosis in a blood vessel or heart valve after it has been treated (as by balloon angioplasty, stenting, or valvuloplasty) with apparent success.

The treatment of a diseased site or lesion with a stent involves both delivery and deployment of the stent. "Delivery" refers to introducing and transporting the stent through a bodily lumen to a region, such as a lesion, in a vessel that requires treatment. "Deployment" corresponds to the expanding of the stent within the lumen at the treatment region. Delivery and deployment of a stent are accomplished by positioning the stent about one end of a catheter, inserting the end of the catheter through the skin into a bodily lumen, advancing the catheter in the bodily lumen to a desired treatment location, expanding the stent at the treatment location, and removing the catheter from the lumen.

In the case of a balloon expandable stent, the stent is mounted about a balloon disposed on the catheter. Mounting the stent typically involves compressing or crimping the stent onto the balloon. The stent is then expanded by inflating the balloon. The balloon may then be deflated and the catheter withdrawn. In the case of a self-expanding stent, the stent may be secured to the catheter via a retractable sheath or a sock. When the stent is in a desired bodily location, the sheath may be withdrawn which allows the stent to self-expand.

The stent must be able to satisfy a number of mechanical requirements. First, the stent must be capable of withstanding the structural loads, namely radial compressive forces, imposed on the stent as it supports the walls of a vessel. Therefore, a stent must possess adequate radial strength. Radial strength, which is the ability of a stent to resist radial compressive forces, is due to strength and rigidity around a circumferential direction of the stent. Radial strength and rigidity, therefore, may also be described as, hoop or circumferential strength and rigidity.

Once expanded, the stent must adequately maintain its size and shape throughout its service life despite the various forces that may come to bear on it, including the cyclic loading induced by the beating heart. For example, a radially directed force may tend to cause a stent to recoil inward. Generally, it is desirable to minimize recoil.

In addition, the stent must possess sufficient flexibility to allow for crimping, expansion, and cyclic loading. Longitudinal flexibility is important to allow the stent to be maneuvered through a tortuous vascular path and to enable it to conform to a deployment site that may not be linear or may be subject to flexure. Finally, the stent must be biocompatible so as not to trigger any adverse vascular responses.

The structure of a stent is typically composed of scaffolding that includes a pattern or network of interconnecting structural elements often referred to in the art as struts or bar arms. The scaffolding can be formed from wires, tubes, or sheets of material rolled into a cylindrical shape. The scaffolding is designed so that the stent can be radially compressed (to allow crimping) and radially expanded (to allow deployment). A conventional stent is allowed to expand and contract through movement of individual structural elements of a pattern with respect to each other. Thus, a stent pattern may be designed to meet the mechanical requirements of a stent described above which include radial strength, minimal recoil, and flexibility.

Stents have been made of many materials such as metals and polymers, including biodegradable polymer materials. Biodegradable stents are desirable in many treatment applications in which the presence of a stent in a body may be necessary for a limited period of time until its intended function of, for example, maintaining vascular patency and/or drug delivery is accomplished. A stent for drug delivery or a medicated stent may be fabricated by coating the surface of either a metallic or polymeric scaffolding with a polymeric carrier that includes an active agent or drug. An agent or drug may also be mixed or dispersed within the polymeric scaffolding.

In general, there are several important aspects in the mechanical behavior of polymers that affect stent design. Polymers tend to have lower strength than metals on a per unit mass basis. Therefore, polymeric stents typically have less circumferential strength and radial rigidity than metallic stents. Inadequate radial strength potentially contributes to a relatively high incidence of recoil of polymeric stents after implantation into vessels.

Another potential problem with polymeric stents is that their struts or bar arms can crack during crimping and expansion, especially for brittle polymers. The localized portions of the stent pattern subjected to substantial deformation tend to be the most vulnerable to failure. Furthermore, in order to have adequate mechanical strength, polymeric stents may require significantly thicker struts than a metallic stent, which results in an undesirably larger profile.

Another potential problem with polymeric stents is long term creep. Long term creep is typically not an issue with metallic stents. Long term creep refers to the gradual deformation that occurs in a polymeric material subjected to an applied load. Long term creep occurs even when the applied load is constant. Long term creep in a polymeric stent reduces the effectiveness of a stent in maintaining a desired vascular patency. In particular, long term creep allows inward radial forces to permanently deform a stent radially inward.

Therefore, it would be desirable to have polymeric stents that provide high radial strength, minimal recoil, and low long term creep.

SUMMARY OF THE INVENTION

Certain embodiments of the present invention include a radially expandable intravascular stent including a plurality of interconnected cells such that at least one of the cells may be a lockable cell. The lockable cell may include a male locking element and a female locking element disposed opposite the male locking element. The male and female locking elements may be movable between an unlocked position and at least one locked position when the stent radially expands. The male locking element and the female locking element each may include at least one set of complementary ratchet elements adapted to engage and lock in at least one locked position.

Certain embodiments of the present invention include a radially expandable intravascular stent including a plurality of radially expandable cylindrical rings that are longitudinally aligned. Each ring may include a plurality of interconnected cells and circumferential links connecting adjacent circumferentially aligned ends of the interconnected cells such that at least one of the cells may include a lockable cell. The lockable cell may include a male locking element and a female locking element disposed opposite the male locking element. The male and female locking elements may be movable between an unlocked position and at least one locked position. The male locking element and the female locking element may include at least one set of complementary ratchet element adapted to engage and lock in at least one locked position.

Certain embodiments of the present invention include a radially expandable intravascular stent including a plurality of interconnected cells such that at least one of the cells may be a lockable cell with a pair of cylindrically aligned ends. The lockable cell may include a first locking element extending into the cell from one side of one of the cylindrically aligned ends and a second locking element extending into the cell toward the first locking element from another side of the cylindrically aligned end. The first and second locking elements may be rotatable towards each other from unlocked positions to locked positions when the stent radially expands. The rotation of the first locking element and the second locking element towards each other may allow the locking elements to engage and lock in at least one locked position.

Certain embodiments of the present invention include a radially expandable intravascular stent including a plurality of interconnected cells such that at least one of the cells may be a lockable cell that may include a first locking element and a second locking element extending into the lockable cell. The first locking element and the second locking element may be adapted to rotate towards each other from unlocked positions to locked positions when the stent radially expands allowing the locking elements to engage and lock in at least one locked position.

Certain embodiments of the present invention include a radially expandable intravascular stent including a plurality of undulating interconnected bar arms including crests formed by bar arms such that at least one of the crests may be a lockable crest that may include a male locking element on one side of the crest and a complementary female locking element disposed opposite the male locking element on another side of the crest. The male and female locking elements may be movable between an unlocked position and at least one locked position as the stent expands and the bar arms that form the crest bend outward.

Certain embodiments of the present invention include a radially expandable intravascular stent including a plurality of interconnected bar arms such that at least two connected bar arms may include a locking mechanism at or adjacent to a region of interconnection of the bar arms. The locking element may include a male locking element on one side of the interconnection region and a complementary female locking element disposed opposite the male locking element on another side of the region. The male and female locking elements may be movable between an unlocked position and a locked position as the stent expands such that an angle between the at least two connected bar arms increases due to rotation of the bar arms outward from the interconnection region.

Certain embodiments of the present invention include a radially expandable intravascular stent including a plurality of interconnected bar arms that may have at least one pair of hingedly connected lockable bar arms connected by a bendable hinge-like bar arm. The pair may include a first bar arm including a male locking element adjacent the bendable bar arm and a second bar arm including a complementary female locking element opposite the male locking element. The male and female locking elements may be movable between an unlocked position and a locked position as the bendable bar arm bends outward due to expansion of the stent such that an angle between the first and second bar arms increases due to rotation of the bar arms outward from the bendable bar arm.

Further embodiments of the present invention include a radially expandable intravascular stent including a plurality of interconnected bar arms including a locking mechanism between at least one pair of bar arms. The bar arms may be adapted to move apart when the stent expands. The locking mechanism may include a locking arm and an actuator arm. The locking arm may be movable from an unlocked position to a locked position when the pair of bar arms moves apart due to expansion of a stent. The actuator arm may be adapted to facilitate movement of the locking arm from the unlocked position to the locked position.

Some embodiments of the present invention include a radially expandable intravascular stent including a plurality of interconnected bar arms that may include a locking mechanism between at least one pair of bar arms that are adapted to move apart when the stent expands. The locking mechanism may include a locking arm and an actuator arm. The actuator arm may be adapted to facilitate movement of the locking arm from an unlocked position to a locked position. The locking arm may be connected at a proximal end to a first bar arm of the pair of bar arms. The actuator arm may be connected at a proximal end to the locking arm. The actuator arm may move the locking arm when the stent expands so that a distal end of the locking arm engages and locks in the locked position at a locking point on the second bar arm.

Certain embodiments of the present invention include a radially expandable intravascular stent including a plurality of interconnected bar arms that may include a locking mechanism between at least one pair of bar arms. The bar arms may be adapted to move apart when the stent expands. The locking mechanism may include a bendable locking arm such that a proximal end of the locking arm may be connected to a first bar arm of a pair of bar arms. A distal end of the locking arm may be connected to a second bar arm of the pair of bar arms. The locking arm may be movable from a bent unlocked position to a locked position when the pair of bar arms move apart due to expansion of a stent. The locking mechanism may further include an actuator arm with a proximal end of the actuator arm connected to the locking arm, the actuator arm adapted to facilitate movement of the locking arm from the unlocked bent position to a locked position when the stent expands.

BRIEF DESCRIPTION OF THE DRAWINGS

FIGS. 4A-B depict embodiments of stent patterns with lockable cells.

DETAILED DESCRIPTION OF THE INVENTION

Figure 3:
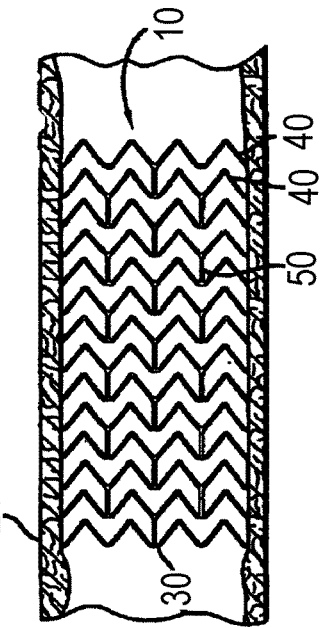
FIG. 3 is an elevation view, partially in section, showing the expanded stent implanted within the artery after withdrawal of the rapid-exchange delivery catheter.

Various embodiments of a stent including locking mechanisms are described herein. These embodiments are particularly useful for stents that are composed in whole or in part of polymers. Polymeric stents tend to be desirable in part because they can provide effective long term treatment without being permanent.

As indicated above, however, there are several potential problems with polymeric stents. Polymers tend to have lower strength than metals on a per unit mass basis. Therefore, polymeric stents have a lower radial strength to resist inward radial compressive forces.

Additionally, another problem with polymeric stents is that most polymers creep when under load and at elevated temperature. In general, creep refers to the increase in strain with time in a polymeric material under a constant load. Long term creep refers to the gradual deformation that occurs in a polymeric material subjected to an applied load. Thus, creep caused by radial compressive forces imposed by a lumen on a stent can effectively reduce the diameter of an implanted stent. The decrease in diameter or recoil thus can possibly lead go malapposition and adverse clinical consequences. Creep is affected by the applied load, the temperature, and the structural integrity of the sample.

One way of increasing the radial strength and reducing or slowing down the effects of creep is to increase the strut width or thickness of a stent pattern. However, increasing the profile of a stent is generally not desirable. The embodiments of stents with locking mechanisms described herein allow an increase in the radial strength of the device and reduction of the effects of creep without changing the width or thickness of the struts of a stent.

As indicated above, stents may be composed partially or completely of polymers. In general, polymers can be biostable, bioabsorbable, biodegradable, or bioerodible. Biostable refers to polymers that are not biodegradable. The terms biodegradable, bioabsorbable, and bioerodable, as well as degraded, eroded, and absorbed, are used interchangeably and refer to polymers that are capable of being completely eroded or absorbed when exposed to bodily fluids such as blood and can be gradually resorbed, absorbed and/or eliminated by the body.

A stent made from a biodegradable polymer is intended to remain in the body for a duration of time until its intended function of, for example, maintaining vascular patency and/or drug delivery is accomplished. After the process of degradation, erosion, absorption, and/or resorption has been completed, no portion of the biodegradable stent, or a biodegradable portion of the stent will remain. In some embodiments, very negligible traces or residue may be left behind. The duration can be in a range from about a month to a few years. However, the duration is typically in a range from about six to twelve months.

The general structure and use of stents will be discussed first in order to lay a foundation for the embodiments of stent patterns herein. In general, stents can have virtually any structural pattern that is compatible with a bodily lumen in which it is implanted. Typically, a stent is composed of a pattern or network of circumferential rings and longitudinally extending interconnecting structural elements of struts or bar arms. In general, the struts are arranged in patterns, which are designed to contact the lumen walls of a vessel and to maintain vascular patency. A myriad of strut patterns are known in the art for achieving particular design goals. A few of the more important design characteristics of stents are radial or hoop strength, expansion ratio or coverage area, and longitudinal flexibility.

Figure 1:
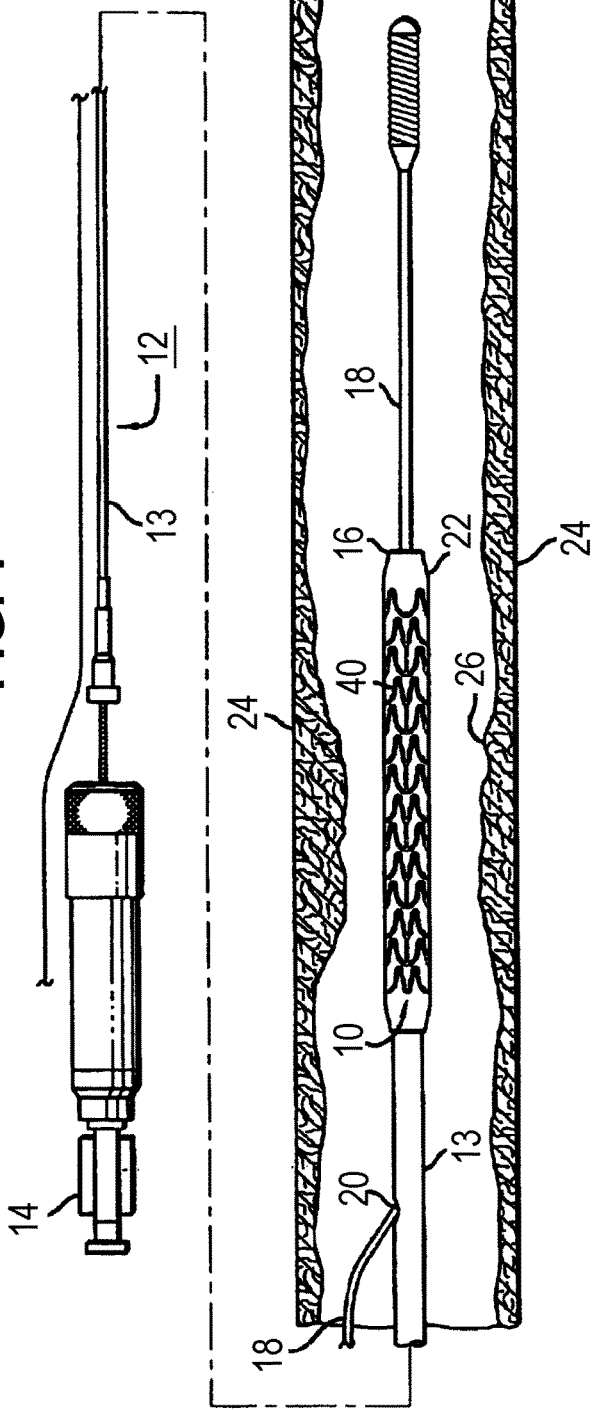
FIG. 1 is an elevation view, partially in section, of a stent which is mounted on a rapid-exchange delivery catheter and positioned within an artery.
Figure 2:
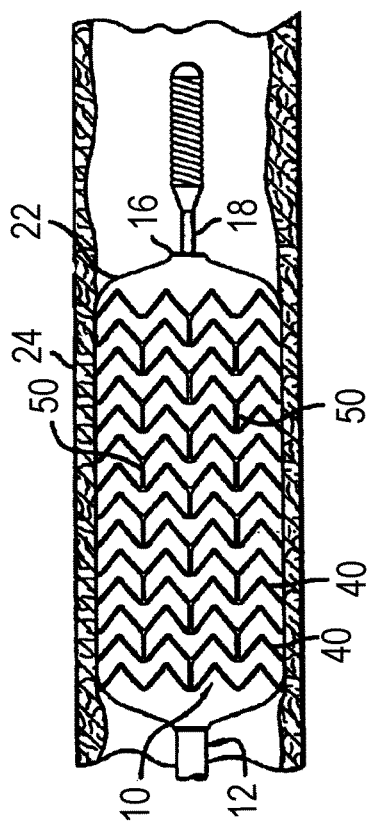
FIG. 2 is an elevation view, partially in section, similar to that shown in FIG. 1, wherein the stent is expanded within the artery so that the stent embeds within the arterial wall.

FIGS. 1-3 can represent any balloon expandable stent 10 with which the various configurations can be used. FIG. 1 depicts a stent 10 with interconnected cylindrical rings 40 mounted on a catheter assembly 12 which is used to deliver stent 10 and implant it in a bodily lumen. Rings 40 are connected by links 50.

For example, a bodily lumen may include a coronary artery, peripheral artery, or other vessel or lumen within the body. The catheter assembly includes a catheter shaft 13 which has a proximal end 14 and a distal end 16. The catheter assembly is configured to advance through the patient's vascular system by advancing over a guide wire by any of the well-known methods of an over-the-wire system (not shown) or a well-known rapid exchange catheter system, such as the one shown in FIG. 1. The stent 10 in FIGS. 1-3 conceptually represents any type of stent well-known in the art, i.e., one having a plurality of cylindrical rings 40.

Catheter assembly 12, as depicted in FIG. 1, includes an RX (rapid-exchange) port 20 where the guide wire 18 exits the catheter. The distal end of guide wire 18 exits catheter distal end 16 so that the catheter advances along the guide wire on a section of the catheter between RX port 20 and catheter distal end 16. As is known in the art, the guide wire lumen which receives the guide wire is sized for receiving various diameter guide wires to suit a particular application. The stent is mounted on an expandable member 22 (e.g., a balloon) and is crimped tightly thereon, so that the stent and expandable member present a low profile diameter for delivery through the arteries.

As shown in FIG. 1, a partial cross-section of an artery 24 has a small amount of plaque that has been previously treated by angioplasty or other repair procedure. Stent 10 is used to repair a diseased or damaged arterial wall as shown in FIG. 1, or a dissection, or a flap, all of which are commonly found in the coronary arteries and other vessels. Stent 10, and embodiments of the stents described herein, also can be placed and implanted without any prior angioplasty.

In a typical procedure to implant stent 10, guide wire 18 is advanced through the patient's vascular system by well-known methods, so that the distal end of the guide wire is advanced past the plaque or a diseased area 26. Prior to implanting the stent, the cardiologist may wish to perform an angioplasty or other procedure (i.e., atherectomy) in order to open and remodel the vessel and the diseased area. Thereafter, stent delivery catheter assembly 12 is advanced over the guide wire so that the stent is positioned in the target area. The expandable member or balloon 22 is inflated by well-known means so that it expands radially outwardly and in turn expands the stent radially outwardly until the stent is apposed to the vessel wall. The expandable member is then deflated and the catheter withdrawn from the patient's vascular system. The guide wire typically is left in the lumen for post-dilatation procedures, if any, and subsequently is withdrawn from the patient's vascular system. As depicted in FIGS. 2 and 3, the balloon is fully inflated with the stent expanded and pressed against the vessel wall. In FIG. 3, the implanted stent remains in the vessel after the balloon has been deflated and the catheter assembly and guide wire have been withdrawn from the patient.

Stent 10 holds open the artery after the catheter is withdrawn, as illustrated by FIG. 3. A stent may be formed from a cylindrical tube with a constant wall thickness, so that the straight and undulating or curved components of the stent are relatively flat in transverse cross-section. Thus, when the stent is expanded, a flat abluminal surface is pressed into the wall of the artery. As a result, the stent does not interfere with the blood flow through the artery. After the stent is pressed into the wall of the artery, it eventually becomes covered with endothelial cell growth which further minimizes blood flow interference. The undulating or curved portion of the stent provides good tacking characteristics to prevent stent movement within the artery. Because cylindrical rings 40 are closely spaced at regular intervals, they provide uniform support for the wall of the artery. Consequently the rings are well adapted to tack up and hold in place small flaps or dissections in the wall of the artery.

The stent locking embodiments disclosed herein are not limited in application to stents. The embodiments may also be applied to implantable medical devices including, but not limited to, self-expandable stents, balloon-expandable stents, stent-grafts, and vascular grafts.

The various embodiments of lockable stents disclosed herein include mechanical locking mechanisms that inhibit or prevent a decrease in diameter of an expanded stent. The locking mechanism may also inhibit or prevent an increase in a radius of an expanded stent beyond a locking radius or position.

Certain embodiments of a radially expandable lockable stent may include a plurality of interconnected cells such that at least one of the cells may be a lockable cell. In some embodiments, the interconnected cells may be arranged in a plurality of radially expandable cylindrical rings that are longitudinally aligned such that each ring includes a plurality of interconnected cells. One embodiment may include circumferential links connecting adjacent circumferentially aligned ends of the interconnected cells.

In one embodiment, adjacent cylindrical rings may be connected by at least one longitudinal link. In one embodiment, at least one longitudinal link may connect longitudinally aligned ends of longitudinally adjacent cells. In another embodiment, at least one longitudinal link may connect adjacent rings between circumferential links on adjacent rings.

Some embodiments may include locking elements disposed at or near opposing longitudinally aligned ends of at least one lockable cell. For example, the lockable cell may be diamond-shaped and the locking elements may be disposed at opposing longitudinally aligned vertices of the lockable cell.

In one embodiment, the lockable cell may be a closed cell. A closed cell refers to a cell that is completely enclosed by bar arms that define the cell with no openings to another cell. In other embodiments, the lockable cell may be open with at least one opening in the bar arms that define the cell. Openings in cells may tend to increase the longitudinal flexibility of a stent.

In some embodiments, the lockable cell may include a male locking element and a female locking element disposed opposite the male locking element. The male and female locking elements may be movable between an unlocked position and at least one locked position when the stent radially expands. In one embodiment, the movement may be circumferentially aligned.

In one embodiment, the male locking element and the female locking element may have at least one set of complementary ratchet elements adapted to engage and lock in at least one locked position. Ratchet elements may include elements protruding from a surface with gaps alternating with the elements such as teeth. One set may correspond to two teeth with a gap in between. At least one locked position may correspond to an expanded radius of the stent. Radial force may be applied to a stent, for example, by a balloon, sufficient to overcome the restraining force of a set of ratchet elements of a locking element. Ratchet elements may be any of a variety of shapes and configurations, such as triangular or square. The locking elements may then engage and lock at least one additional set of ratchet elements as the locking elements move from at least one locked position to another locked position at a larger stent radius as the stent expands.

FIG. 4A depicts one embodiment of a stent pattern 100 with lockable cells 104. In FIG. 4A, stent pattern 100 is shown in a flattened condition so that the pattern can be clearly viewed. When the flattened portion of stent pattern 100 is in a cylindrical condition, it forms a stent.

Lockable cells 104 are arranged in radially expandable cylindrical rings 108. Lockable cells are closed since there is no opening in the bar arms that form the cells. For reference, line A-A represents the longitudinal axis of a stent of the pattern depicted in FIG. 4A. Cells 104 are diamond-shaped and are connected circumferentially by circumferential links 112. Longitudinal links 116 connect adjacent rings by connecting circumferential links of adjacent rings.

Lockable cells 104 include a male locking element 120 and a female locking element 124 at opposite circumferentially aligned ends of cell 104. Male locking element 120 has sets of teeth 128 and female locking element 124 has complementary sets of teeth 132. When a stent with stent pattern 100 is expanded, the lockable cells 104 elongate circumferentially. Thus, male locking element 120 and female locking element 124 move toward one another and engage and lock. At least one set of teeth 128 and 132 engage and lock the stent in an expanded radius. Teeth 128 and 132 are inclined in a direction opposite to the movement of locking elements 120 and 124 to inhibit or prevent reverse movement of the locking movements.

As the stent expands further, male locking element 120 and female locking element 124 continue to move toward one another. When sufficient radial force is applied to the stent, the locking force of the teeth is overcome and additional sets of teeth 128 and 132 engage and lock the stent at larger radii. Engagement of each additional set of teeth 128 and 132 allow locking of the stent at various expanded radii. Locking elements 120 and 124 inhibit recoil of the stent below an expanded radius.

Since an addition radial force must be applied to engage additional locking elements, locking elements 120 and 124 also inhibit or prevent further expansion at a locked radius.

In one embodiment, lockable cells may include a pair of centering elements movably disposed within the lockable cell. The pair of centering elements may be adapted to center the locking elements along an axis of movement of the locking elements from the unlocked position to the locked position. As shown in FIG. 4A, lockable cells 104 include centering elements 136 which protrude into the cells 104 adjacent to opposing cylindrically aligned ends of cells 104.

As a stent with stent pattern 100 expands, centering elements 104 move toward each other and the locking elements 120 and 124. Centering elements 104 make contact with locking elements 120 and 124 and inhibit movement of the locking elements out of circumferential alignment.

Figure 4B:
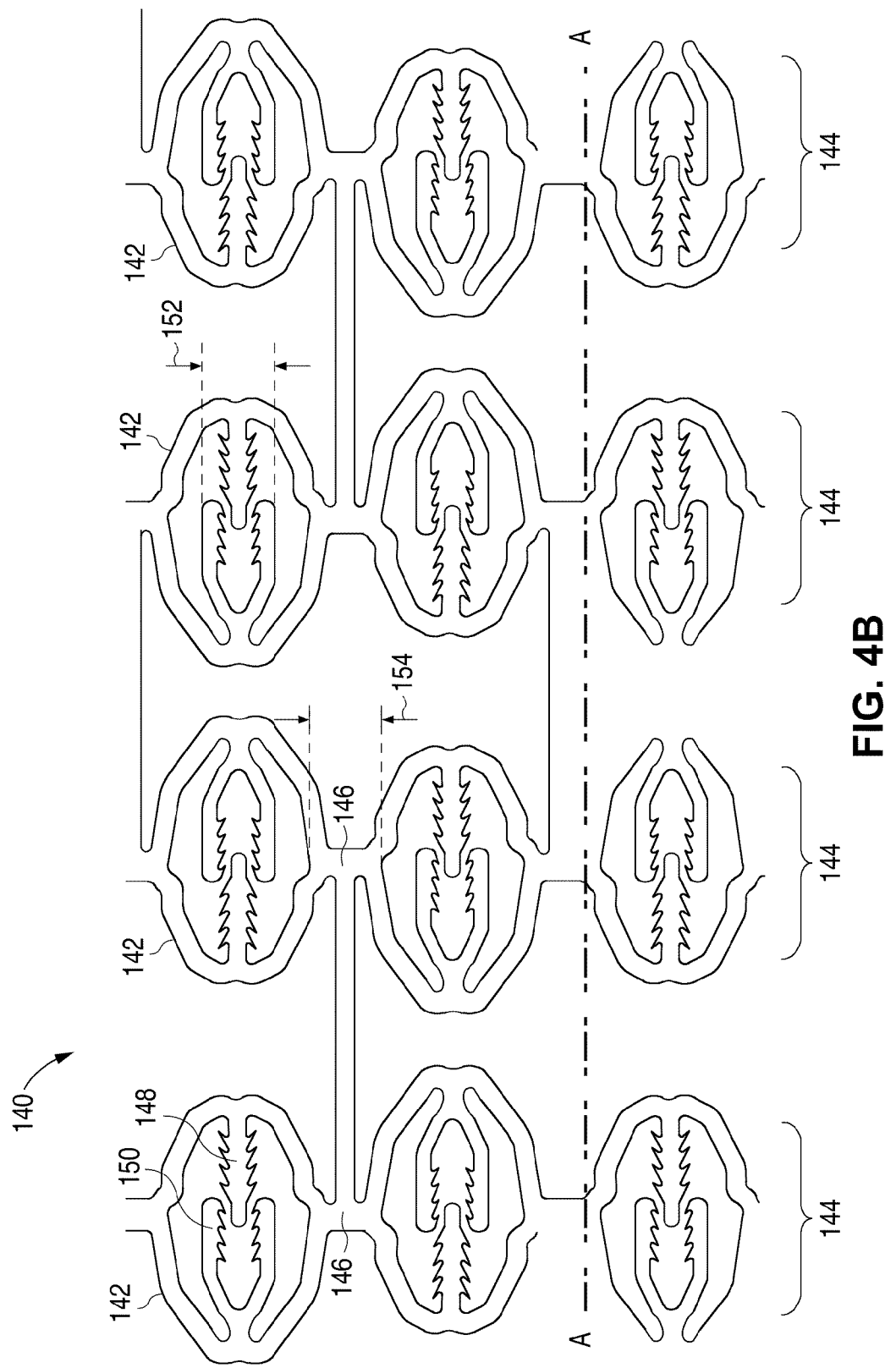

FIG. 4B depicts a stent pattern 140 similar to stent pattern 100 in FIG. 4A with lockable cells 142 arranged in cylindrical rings 144. Stent pattern 140 is also shown in a flattened condition. Lockable cells include male locking element 148 and female locking element 150. A width 152 of female locking element 150 shown is larger than a width of female locking element 104 in FIG. 4A. Circumferential links 146 with a length 154 are longer than links 112 in FIG. 4A.

Figure 5:
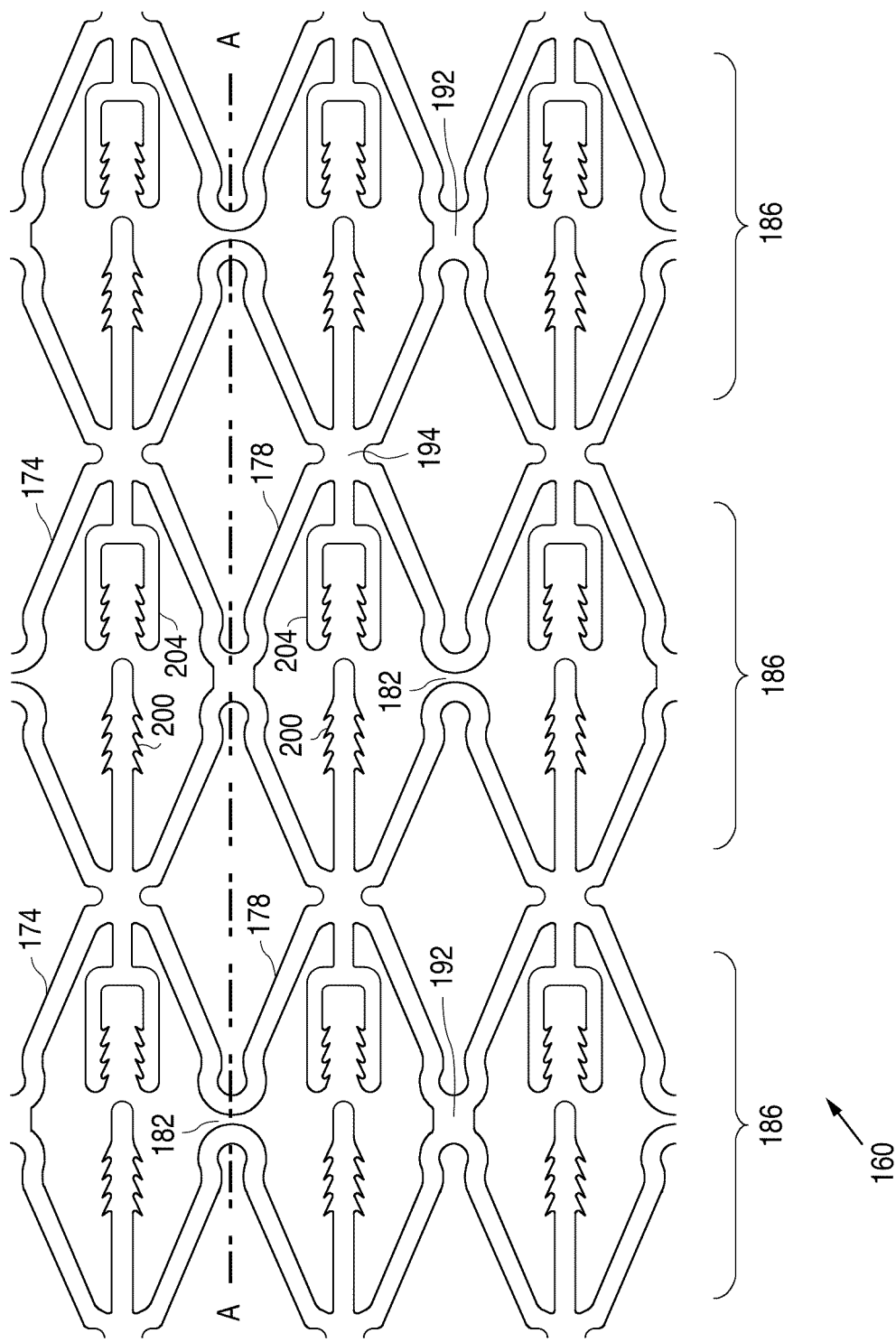
FIG. 5 depicts a stent pattern with pairs of open lockable cells.

FIG. 5 depicts a stent pattern 160 with pairs of lockable cells 174 and 178. Stent pattern 160 is also shown in a flattened condition. Each lockable cell of the pair of lockable cells 174 and 178 has an opening 182 at a shared cylindrically aligned end. Opening 182 allows for greater longitudinal flexibility.

Lockable cells 174 and 178 are arranged in radially expandable cylindrical rings 186. For reference, line A-A represents the longitudinal axis of a stent of the pattern depicted in FIG. 5.

Circumferentially adjacent pairs of lockable cells 174 and 178 are connected by circumferential links 192. Lockable cells 174 and 178 are connected end-to-end by longitudinal links 192 that connect longitudinally aligned ends of circumferentially adjacent cells.

Lockable cells 174 and 178 include male and female locking elements 200 and 204. As the stent expands, locking elements 200 and 204 move towards each other and then lock and engage at one or more stent radii, as described above.

Additional embodiments of a radially expandable lockable stent may include a plurality of interconnected cells having a pair of cylindrically aligned ends such that at least one of the cells may be include rotatable locking elements. In some embodiments, the lockable cell may include a rotatable first locking element and a rotatable second locking element. The first locking element may extend into the cell on one side of one of the cylindrically aligned ends. The second locking element may extend toward the first locking element into the cell from another side of the cylindrically aligned end. In an embodiment, the first and the second locking elements may extend obliquely to the longitudinal axis into of the stent such that the locking elements are aligned towards each other.

In an embodiment, the first and second locking elements may be rotatable towards each other from unlocked positions to locked positions when the stent radially expands. The rotation of the first locking element and the second locking element towards each other allows the locking arms to engage and lock in at least one locked position.

In an embodiment, the lockable cell may be diamond-shaped with the cylindrically aligned ends being opposing vertices. The plurality of cells may be arranged in a plurality of radially expandable cylindrical rings. The lockable cell may be a closed or an open cell.

In some embodiments, the locking elements may be locking arms having hook-like elements that engage and lock when the stent expands. The hook-like elements may be disposed at or near ends of the locking arms. In some embodiments, each of the locking elements may include more than one hook-like element so that the locking elements may lock the stent at more than one expanded radius. In other embodiments, the first locking element may have a male end and the second locking element may have a complementary female end adapted to engage and lock when the stent expands.

Figure 6:
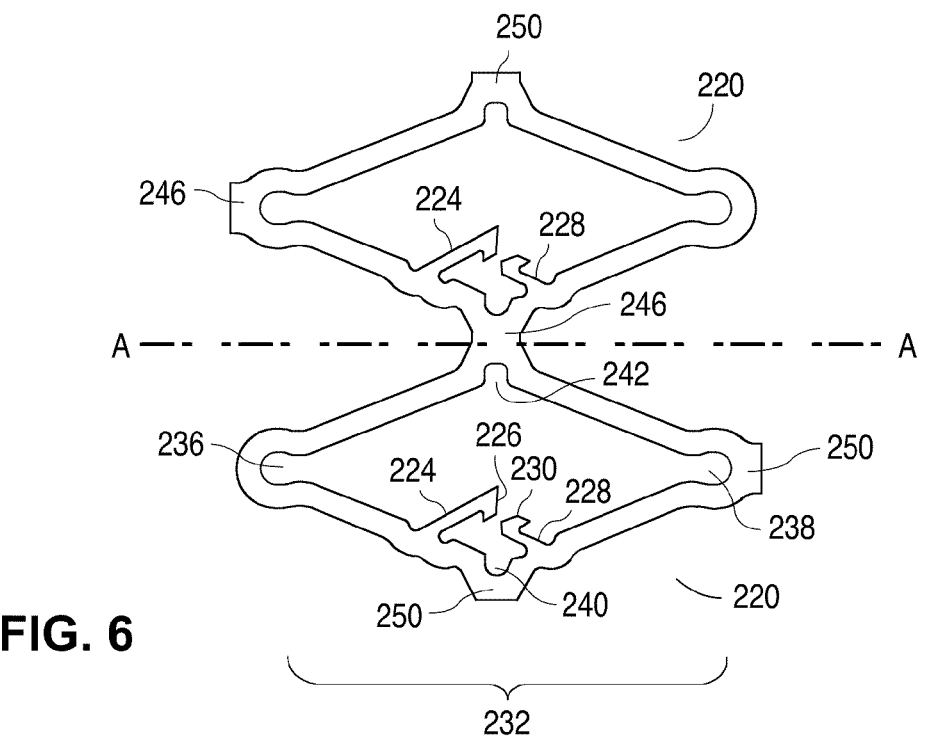
FIG. 6 depicts lockable cells with rotatable locking elements.

FIG. 6 depicts an embodiment of lockable cells 220 with rotatable locking arms 224 and 228. Locking arms 224 and 228 have hooks 226 and 230 that are configured to engage and lock. In FIG. 6, lockable cells are shown in a flattened condition so that the cells can be clearly viewed.

As indicated above, lockable cells 220 are a portion of a radially expandable cylindrical ring 232. Lockable cells 220 are closed since as there is no opening in the bar arms that form the cells. For reference, line A-A represents the longitudinal axis of a stent of the pattern depicted in FIG. 6. Cells 220 are diamond-shaped with longitudinally aligned ends 236 and 238 and circumferentially aligned ends 240 and 242. Cells 220 are connected circumferentially by circumferential links 246. Longitudinal links 250 connect adjacent rings by connecting longitudinal ends of adjacent rings.

Locking arm 224 extends into a cell 220 from one side of end 240. Locking arm 228 extends toward locking arm 224 from the other side of end 240. When a stent with lockable cells 220 is expanded, lockable cells 200 elongate circumferentially. As a result, locking elements 224 and 228 rotate in oppositely directions towards each other from an unlocked position to a locked position. Hooks 226 and 230 engage and lock in a locked position.

Figure 7:
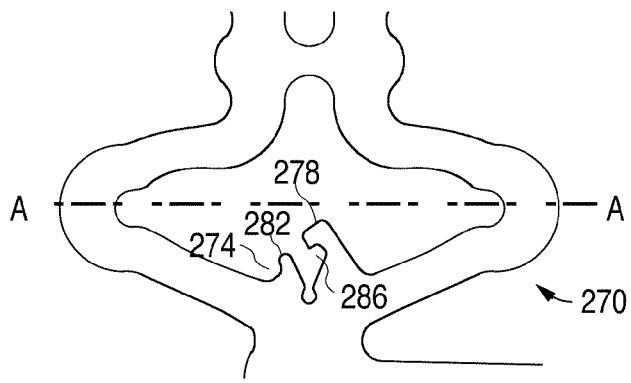
FIG. 7 depicts a lockable cell with rotatable locking elements.

FIG. 7 depicts another embodiment of a lockable cell with rotatable locking elements. In FIG. 7, lockable cell 270 has locking elements 274 and 278. Line A-A represents the longitudinal axis of a stent with lockable cell 270. Locking elements 274 and 278 are on either side of a longitudinal end. Locking element 274 has a male end 282 and locking element 278 has a female end 286. When a stent with lockable cells 270 is expanded, lockable cells 270 elongate circumferentially. As a result, locking elements 274 and 278 rotate in opposite directions towards each other from an unlocked position to a locked position. Male end 282 engages female end 278 and locks in a locked position.

Other embodiments of lockable stents patterns may include a plurality of interconnected bar arms with at least two connected bar arms having a locking mechanism at or adjacent to a region of interconnection of the connected bar arms. The interconnection region may correspond to a crest formed by a pair of bar arms.

In one embodiment, the locking mechanism may include a male locking element on one side of the interconnection region and a complementary female locking element disposed opposite the male locking element on another side of the region. The male and female locking elements may be movable between an unlocked position and a locked position as the stent expands such that an angle between the at least two connected bar arms increases due to rotation of the bar arms outward from the interconnection region. In one embodiment, the locked elements inhibit expansion of the stent beyond a locked radius.

In some embodiments, the plurality of interconnected bar arms may include at least one pair of hingedly connected lockable bar arms connected by a bendable hinge-like bar arm. The pair may include a first bar arm and a second bar arm. The first bar arm may include a male locking element adjacent the bendable bar arm. The second bar arm may include a complementary female locking element opposite the female locking element. The male and female locking elements may be movable between an unlocked position and a locked position as the bendable bar arm bends outward due to expansion of the stent such that an angle between the first and second bar arms increases due to rotation of the bar arms outward from the bendable bar arm.

In one embodiment, the male locking element may include a curved member and the female locking element may be a member having a complementary curved slot. The curved member and slot may approximately follow the curvature of a crest. As a stent expands, the angle between the bar arms increases and the curved member may engage the slot and then lock.

In another embodiment, the male locking element may be a straight or substantially straight member and the female member may be a complementary member having a straight or substantially straight slot.

In some embodiments, the male locking element and the female locking element may include ratchet elements adapted to engage and lock in at least one locked position. In one embodiment, the male and the female locking elements may each include two complementary locking surfaces. The male locking element may include ratchet elements on at least one locking surface. The female locking element may also include complementary ratchet elements on at least one corresponding female locking surface.

Figure 8:
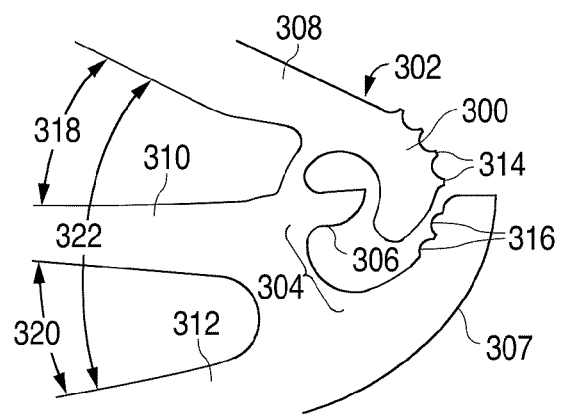
FIG. 8 depicts a locking mechanism at a region of interconnection of bar arms.

FIGS. 8-12 depict an embodiment of locking mechanisms at or adjacent to a region of interconnection 302 of a pair of bar arms. FIG. 8 depicts a locking mechanism with a male locking element 300 and female locking element 304 at region of interconnection 302 of bar arms 308, 310, and 312. Female locking element 304 is formed by a member 306, near the center of interconnection region 302, and member 307. Male locking element 300 has ratchet elements or teeth 314 on one locking surface and female locking element 304 has complementary ratchet elements 316 on one locking surface.

As a stent having a locking mechanism shown in FIG. 8 expands, the male and female locking elements move from an unlocked position as shown to a locked position. Bar arms 308 and 312 rotate outward from interconnection region 302 so that angles 318, 320, and 322 increase. Locking elements 300 and 304 engage and lock the stent in an expanded radius. More than one set of ratchet elements 314 and 316 allow a stent to be locked at more than one radii.

Figure 9:
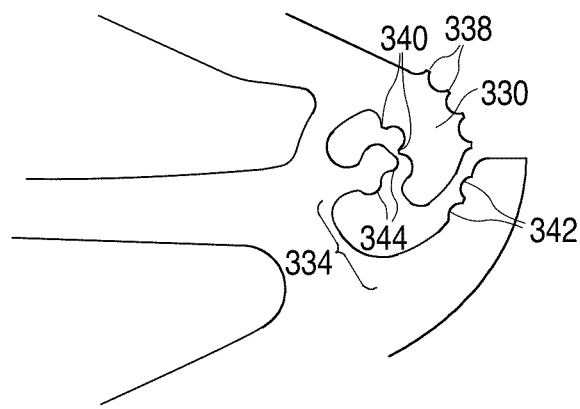
FIG. 9 depicts a locking mechanism at a region of interconnection of bar arms.

FIG. 9 depicts a locking mechanism similar to that illustrated in FIG. 8. The locking mechanism includes a male locking element 330 and a female locking element 334. Male locking element 330 has ratchet elements or teeth 338 on one locking surface and ratchet elements or teeth 340 on another locking surface. Female locking element 334 includes complementary ratchet elements or teeth 342 and 344.

Figure 10:
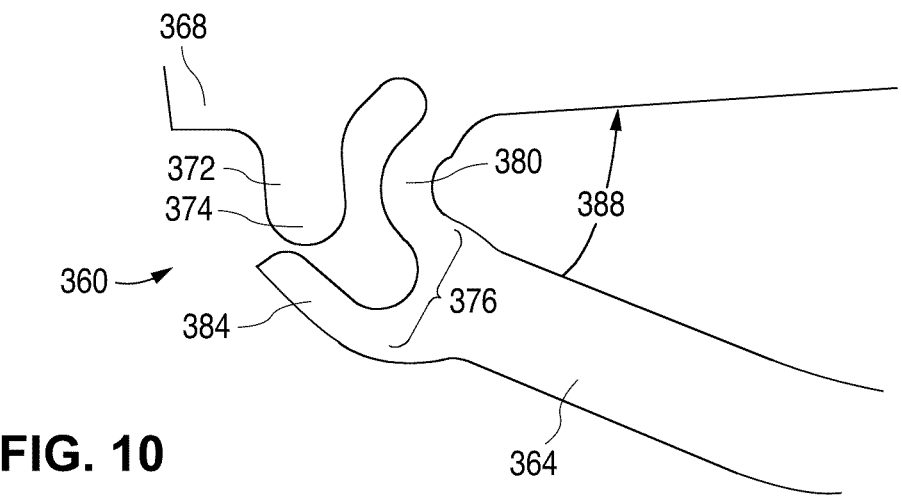
FIG. 10 depicts a locking mechanism at a region of interconnection of bar arms.

FIG. 10 depicts an embodiment of a locking mechanism at an interconnection region 360 between hingedly connected two bar arms, 364 and 368 connected by bendable hinge-like bar arm 380. The locking mechanism includes a male locking element 372 and a female locking element 376. Male locking element 372 is substantially straight with a curved end section 374. Complementary female locking element 376 is formed by a part of bar arm 380 and member 384.

As a stent expands, bar arm 380 bends and bar arms 364 and 368 rotate outward so that angle 388 increases. Locking elements 372 and 376 engage and lock the stent in an expanded radius.

Figure 11:
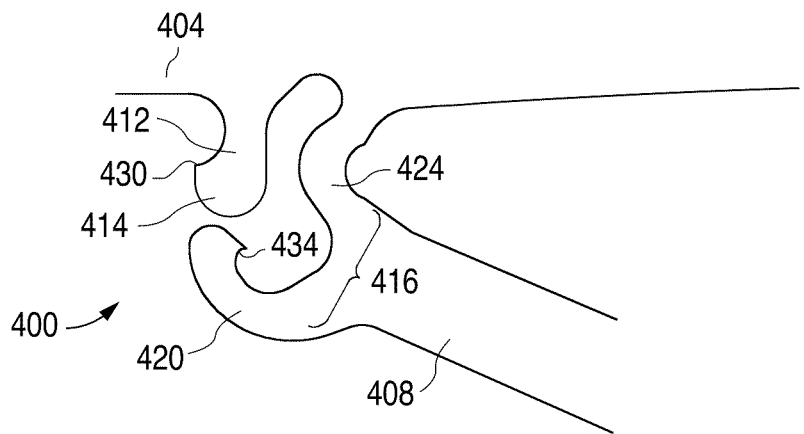
FIG. 11 depicts a locking mechanism at a region of interconnection of bar arms.

FIG. 11 depicts another locking mechanism at an interconnection region 400 between two hingedly connected two bar arms, 404 and 408 connected by bendable hinge-like bar arm 424. The locking mechanism includes a male locking element 412 and a female locking element 416. Male locking element 412 includes an end section 414 that is wider than the remainder of element 412 to facilitate locking. Complementary female locking element 416 is formed by a member 420 and part of bar arm 424. End section 414 includes a lip 430 that can engage a notch 434 in member 420 to facilitate locking.

Figure 12:
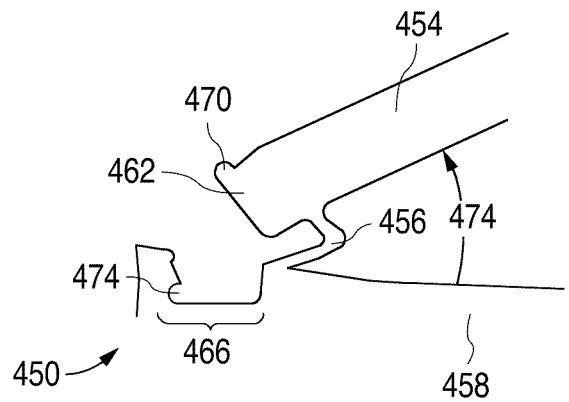
FIG. 12 depicts a locking mechanism at a region of interconnection of bar arms.

FIG. 12 depicts a locking mechanism at an interconnection region 450 between two bar arms, 454 and 458 hingedly connected by a v-shaped bar arm 454. A male locking element 462 is substantially straight and includes an end section of bar arm 454. Female locking element 466 is a rectangular slot within bar arm 458. Male locking element 462 includes a lip 470 and female locking element 466 has a complementary notch 474 to facilitate locking. As a stent expands, bar arm 456 allows bar arms 454 and 458 to rotate outward so that angle 474 increases and locking element 462 engages and locks in locking element 466.

In further embodiments, a stent may have a locking mechanism between a pair of bar arms that are adapted to move apart when a stent expands. For instance, the locking mechanism may be between a bending portion, such as a v-shaped element, of a stent formed by a pair of bar arms that form a v-shaped element. The bending portion or v-shaped element may be configured to bend outward when a stent expands. The locking mechanism may include a locking arm and an actuator arm. The actuator arm may facilitate movement of a locking arm from an unlocked position to a locked position. The locking arm may lock a stent in an expanded configuration.

In some embodiments, a locking mechanism between at least one pair of bar arms that are adapted to move apart when a stent expands may include a bendable locking arm. The locking arm may be bendable at a point between a distal end and proximal end of the locking arm. In one embodiment, a proximal end of the locking arm may be connected to a first bar arm of a pair of bar arms and a distal end of the locking arm may be connected to a second bar arm of the pair of bar arms. For instance, the first and second bar arms may form a bending portion, such as a v-shaped element, that may be configured to bend outward when a stent expands.

Furthermore, the locking arm may be movable from a bent unlocked position to a locked position when the pair of bar arms moves apart as the stent expands. In one embodiment, the locking arm may include a pair of hingedly connected bar arms that are adapted to rotate from a bent unlocked position to the locked position. The locking mechanism between at least one pair of bar arms may lock the stent in an expanded configuration. In one embodiment, the locking element may be cylindrically or substantially cylindrically aligned when in the locked position.

In addition, the locking mechanism may also include an actuator arm. The actuator arm may be adapted to facilitate movement of the locking arm from the unlocked bent position to a locked position when the stent expands. A proximal end of the actuator arm may be connected to the locking arm. A distal end of the actuator arm may be connected to a portion of the stent, for example, a third bar arm, adjacent to the locking mechanism. The adjacent portion may move as the stent expands, allowing the actuator arm to facilitate movement of the locking arm. In one embodiment, the first and second bar arm may be on one ring of a plurality of cylindrical rings and the adjacent portion may be a bar arm on an adjacent ring.

Figure 13:
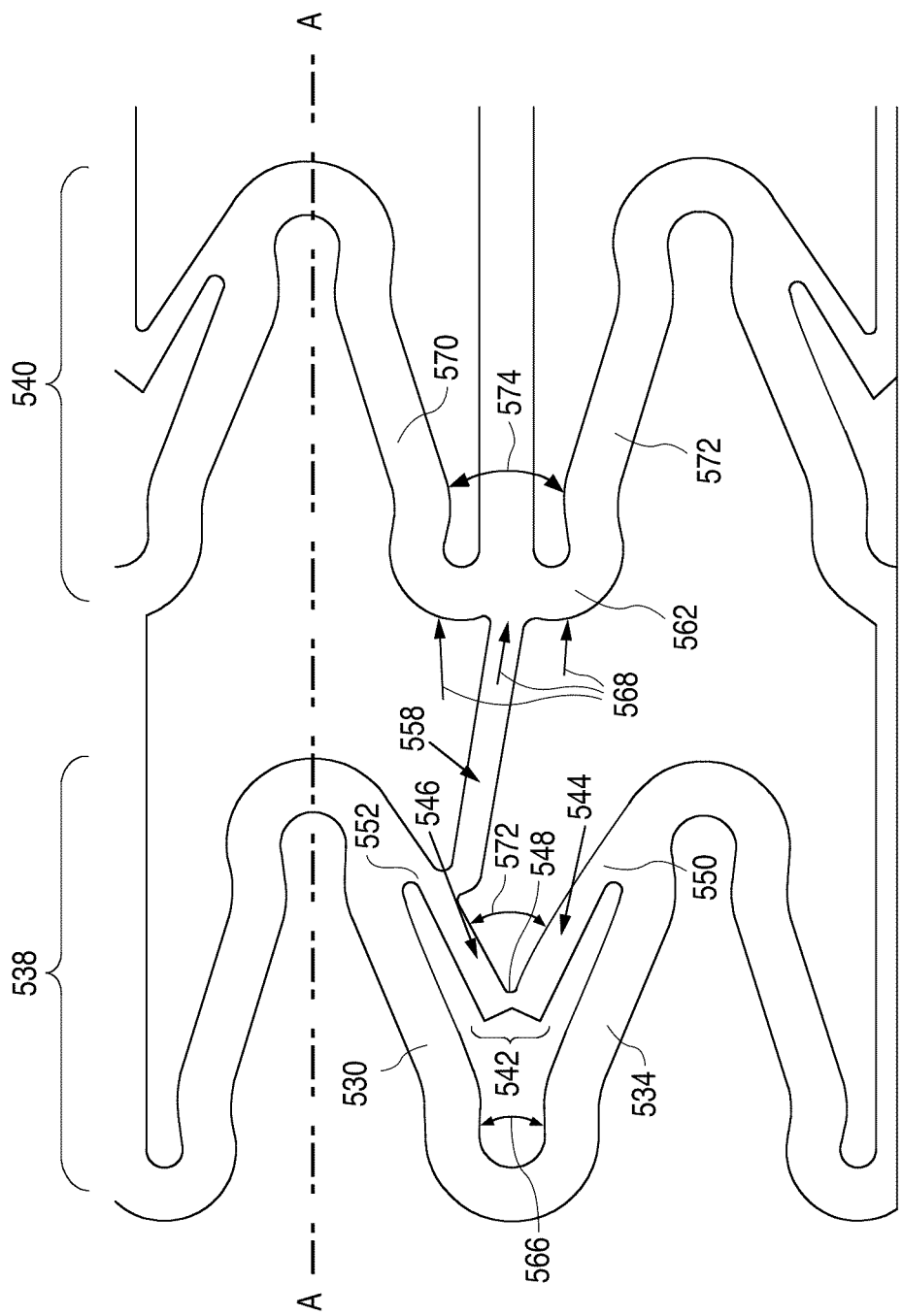
FIG. 13 depicts a locking mechanism with an actuator arm and locking arm.

FIG. 13 depicts a locking mechanism for a stent in a v-shaped or bending portion of a stent formed by bar arms 530 and 534. The stent has a pattern including radially expandable cylindrical rings including rings 538 and 540. The locking mechanism includes a locking arm 542 that is composed of bar arms 544 and 546 that are hingedly connected at a location 548 at or near the midpoint of locking arm 542. An end 550 of locking arm 542 is connected to bar arm 534 and end 552 of locking arm 542 is connected to bar arm 530. An actuator arm 558 is connected to bar arm 546 of locking arm 542 and a bar arm 562 on an adjacent ring 540.

As the stent expands, bar arms 530 and 534 move apart as shown by an arrow 566. Bar arms 570 and 572 also move apart as shown by an arrow 574 which also causes bar arm 562 to move as shown by arrows 568. Actuator arm 558 moves as shown by arrows 568 and pulls locking arm 542 into a straight locked position as shown by an arrow 572.

Another embodiment of a locking mechanism between at least one pair of bar arms that are adapted to move apart when the stent expands may include an actuator arm and a locking arm with an end that engages and locks in a locked position. The actuator arm may be adapted to facilitate movement of the locking arm from an unlocked position to a locked position. The locking arm may be connected at a proximal end to a first bar arm of the pair of bar arms. The distal end of the locking arm may be free floating, i.e., not connected when in an unlocked position.

Additionally, in one embodiment, the actuator arm may be connected at a proximal end to the locking arm. The proximal end of the actuator arm may be connected to the locking arm at a location between the distal end and the proximal end of the locking arm. For example, the location may be at or near a midpoint between the distal end and proximal end of the locking arm. The actuator arm may move the locking arm when the stent expands so that a distal end of the locking arm engages and locks in the locked position at a locking point on the second bar arm.

In one embodiment, a distal end of the actuator arm may be connected to a portion of the stent that is adjacent to the locking mechanism. For example, the actuator arm may be a third bar arm that may pull the actuator arm when the stent expands in a way that allows the actuator arm to move the locking arm from the unlocked to the locked position. The adjacent portion may move as the stent expands, allowing the actuator arm to facilitate movement of the locking arm. In one embodiment, the first and second bar arm may be on one ring of a plurality of cylindrical rings and the adjacent portion may be a bar arm on an adjacent ring.

In an embodiment, the actuator arm may move the locking arm so that its free floating distal end engages and locks at a locking point on the second bar arm. Thus, a distal end of the locking arm in the locked position may be engaged and locked at the locking point on the second bar arm. In an embodiment, the locking point may be a depression in the second bar arm such that the distal end of the locking arm is adapted to engage and lock in the depression or slot.

In some embodiments, the second bar arm may include two or more locking points so that the locking mechanism has more than one locked position. Thus, the stent may be expanded and locked at more than one radius.

The locking mechanism between at least one pair of the bar arms may lock the stent in an expanded configuration. In one embodiment, the locking arm of the locking element may be cylindrically or substantially cylindrically aligned when in the locked position.

Figure 14:
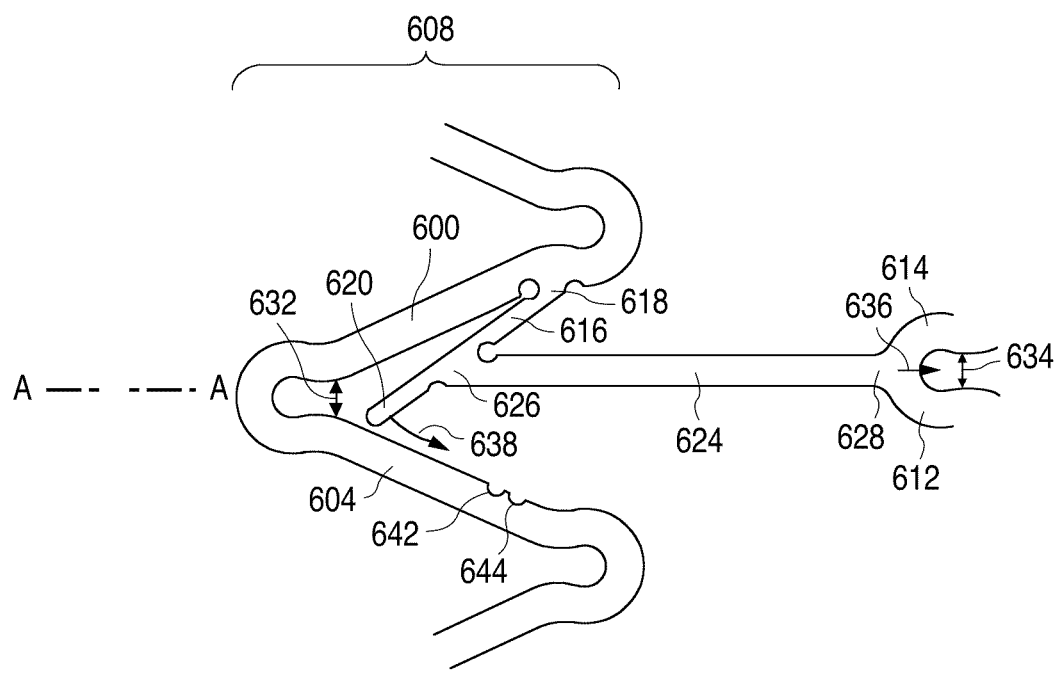
FIG. 14 depicts a locking mechanism with an actuator arm and locking arm.

FIG. 14 depicts a locking mechanism in a v-shaped or bending portion of a stent formed from bar arms 600 and 604. The stent has a pattern including radially expandable cylindrical rings including ring 608. For reference, line A-A represents the longitudinal axis of a stent with the locking mechanism. A portion of bar arms 612 and 614 of an adjacent ring is shown. The locking mechanism includes a locking arm 616. A proximal end 618 of locking arm 616 is connected to bar arm 600 and a distal end 620 of locking arm 616 is free floating. An actuator arm 624 is connected at a proximal end 626 to locking arm 616 at or near a midpoint between proximal end 618 and distal end 620. Actuator arm 624 is connected at a distal end 628 to bar arms 612 and 614.

As the stent expands, bar arms 600 and 604 move apart as shown by an arrow 632. Bar arms 612 and 614 also move apart as shown by an arrow 634 which also causes bar arms 612 and 614 to move as shown by arrow 636. Actuator arm 624 moves as shown by arrow 636 and pulls locking arm 616 as shown by an arrow 638 so that free floating distal end 620 of locking arm 616 engages and locks at a locking point 642. Expansion of the stent further causes distal end 620 of locking arm 616 to engage and lock at a locking point 644.

Stents with the embodiments of locking mechanisms disclosed herein may be formed from a polymeric tube by laser cutting the pattern of struts in the tube. The stent may also be formed by laser cutting a polymeric sheet, rolling the pattern into the shape of the cylindrical stent, and providing a longitudinal weld to form the stent. Other methods of forming stents are well known and include chemically etching a polymeric sheet and rolling and then welding it to form the stent.

Polymer tubes used for fabricating stents may be formed by various methods. These include, but are not limited to, extrusion and injection molding. A tube used for fabricating a stent may be cylindrical or substantially cylindrical in shape. Conventionally extruded tubes tend to possess no or substantially no radial orientation or, equivalently, polymer chain alignment in the circumferential direction. In some embodiments, the diameter of the polymer tube prior to fabrication of an implantable medical device may be between about 0.2 mm and about 5.0 mm, or more narrowly between about 1 mm and about 3 mm.

Representative examples of polymers that may be used to fabricate embodiments of implantable medical devices disclosed herein include, but are not limited to, poly(N-acetylglucosamine) (Chitin), Chitosan, poly(3-hydroxyvalerate), poly(lactide-co-glycolide), poly(3-hydroxybutyrate), poly(4-hydroxybutyrate), poly(3-hydroxybutyrate-co-3-hydroxyvalerate), polyorthoester, polyanhydride, poly(glycolic acid), poly(glycolide), poly(L-lactic acid), poly(L-lactide), poly(D,L-lactic acid), poly(D,L-lactide), poly(L-lactide-co-D,L-lactide), poly(caprolactone), poly(L-lactide-co-caprolactone), poly(D,L-lactide-co-caprolactone), poly(glycolide-co-caprolactone), poly(trimethylene carbonate), polyester amide, poly(glycolic acid-co-trimethylene carbonate), co-poly(ether-esters) (e.g. PEO/PLA), polyphosphazenes, biomolecules (such as fibrin, fibrinogen, cellulose, starch, collagen and hyaluronic acid), polyurethanes, silicones, polyesters, polyolefins, polyisobutylene and ethylene-alphaolefin copolymers, acrylic polymers and copolymers other than polyacrylates, vinyl halide polymers and copolymers (such as polyvinyl chloride), polyvinyl ethers (such as polyvinyl methyl ether), polyvinylidene halides (such as polyvinylidene chloride), polyacrylonitrile, polyvinyl ketones, polyvinyl aromatics (such as polystyrene), polyvinyl esters (such as polyvinyl acetate), acrylonitrile-styrene copolymers, ABS resins, polyamides (such as Nylon 66 and polycaprolactam), polycarbonates, polyoxymethylenes, polyimides, polyethers, polyurethanes, rayon, rayon-triacetate, cellulose, cellulose acetate, cellulose butyrate, cellulose acetate butyrate, cellophane, cellulose nitrate, cellulose propionate, cellulose ethers, and carboxymethyl cellulose. Additional representative examples of polymers that may be especially well suited for use in fabricating embodiments of implantable medical devices disclosed herein include ethylene vinyl alcohol copolymer (commonly known by the generic name EVOH or by the trade name EVAL), poly(butyl methacrylate), poly(vinylidene fluoride-co-hexafluoropropene) (e.g., SOLEF 21508, available from Solvay Solexis PVDF, Thorofare, N.J.), polyvinylidene fluoride (otherwise known as KYNAR, available from ATOFINA Chemicals, Philadelphia, Pa.), ethylene-vinyl acetate copolymers, poly(vinyl acetate), styrene-isobutylene-styrene triblock copolymers, and polyethylene glycol.

EXAMPLES

Embodiments of the present invention is illustrated by the following set forth examples. All parameters and data are not to be construed to unduly limit the scope of the embodiments of the invention.

Example 1

Figure 15:
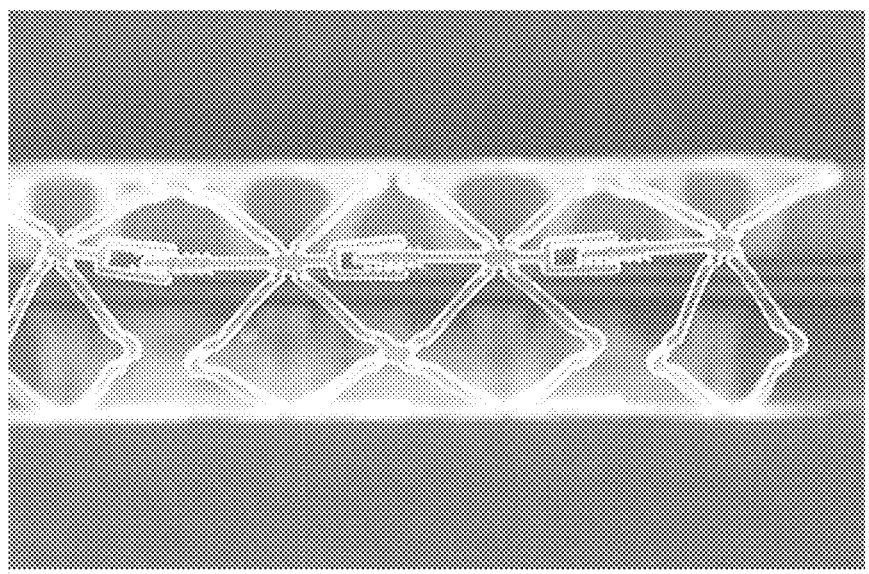
FIG. 15 is an optical micrograph of an expanded stent with the locking elements engaged.
Figure 16:
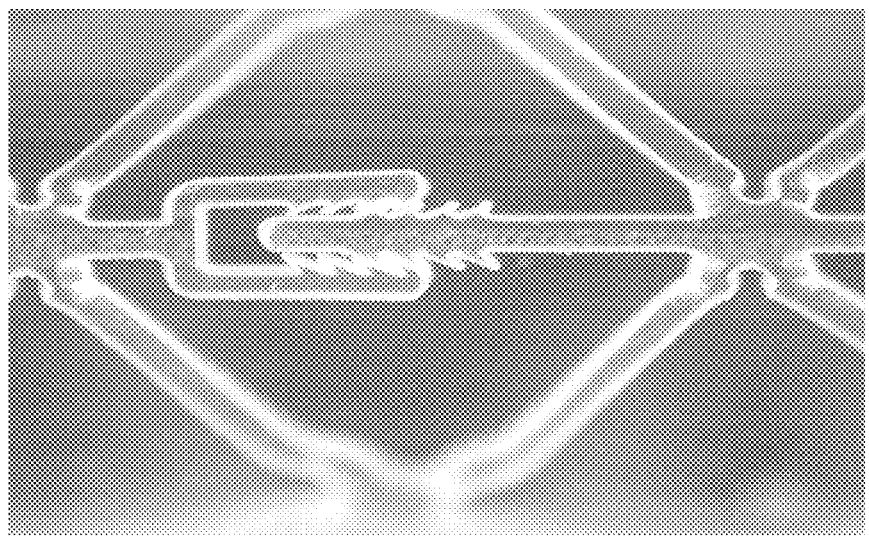
FIG. 16 depicts an optical micrograph of a cell of the stent of FIG. 15 with engaged locking elements.

A stent with a stent pattern shown in FIG. 5 was tested. Stents were cut from 5 percent crystallinity poly (L-lactic acid) tubes. Prior to forming the stent pattern, the tubes were radially expanded. The stents were loosely mounted (crimped) on 5.0×12 mm LeMans catheters. The mounted stents were soaked for 30 seconds in 37° C. water. The stents were first deployed (expanded) at 8 atmospheres. The locks did not engage at 8 atmospheres. The pressure was then increased to 10, 12, 18, and 20 atmospheres. The locks began to engage at 12 atmospheres. FIG. 15 is an optical micrograph of the expanded stent at 12 atmospheres with the locking elements engaged. FIG. 16 depicts an optical micrograph of a cell with engaged locking elements of the stent depicted in FIG. 15. The micrographs indicated that the bar arms do not travel far enough to push the locks together.

Example 2

A stent with a stent pattern shown in FIG. 4A was tested. Width 152 of female locking elements 150 is 0.022 inch and length 154 of links 146 is 0.022 inch. When this pattern is crimped onto a balloon, the resulting diameter is 0.056 inch.

Figure 17:
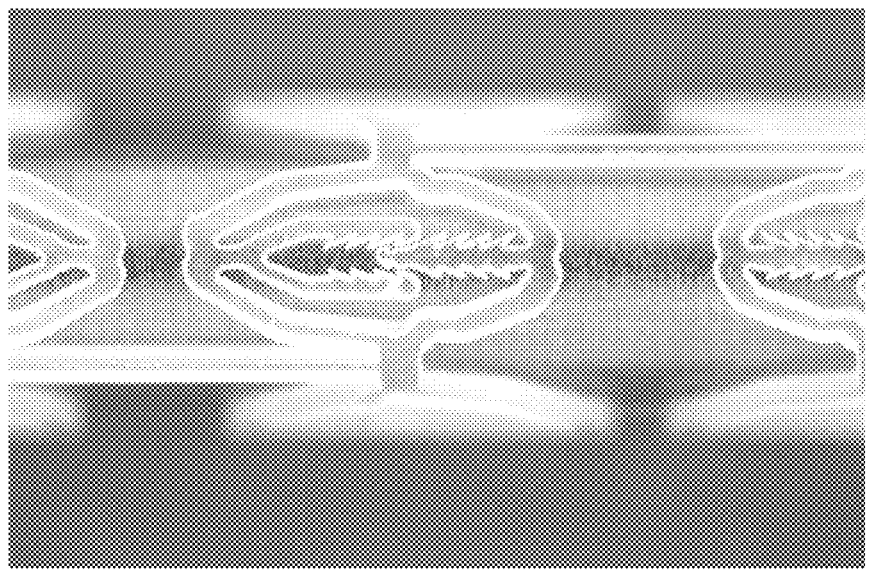
FIG. 17 depicts an optical micrograph of a stent prior to deployment.

The stents were loosely mounted (crimped) on 2.75×12 mm and 3.5×12 mm LeMans catheters. The units were soaked for 60 seconds in 37° C. water. The samples were deployed at 6 atmospheres pressure for the 3.5 mm sample and 5 atmospheres for the 2.75 mm sample. FIG. 17 depicts an optical micrograph of the stent prior to deployment.

Figure 18:
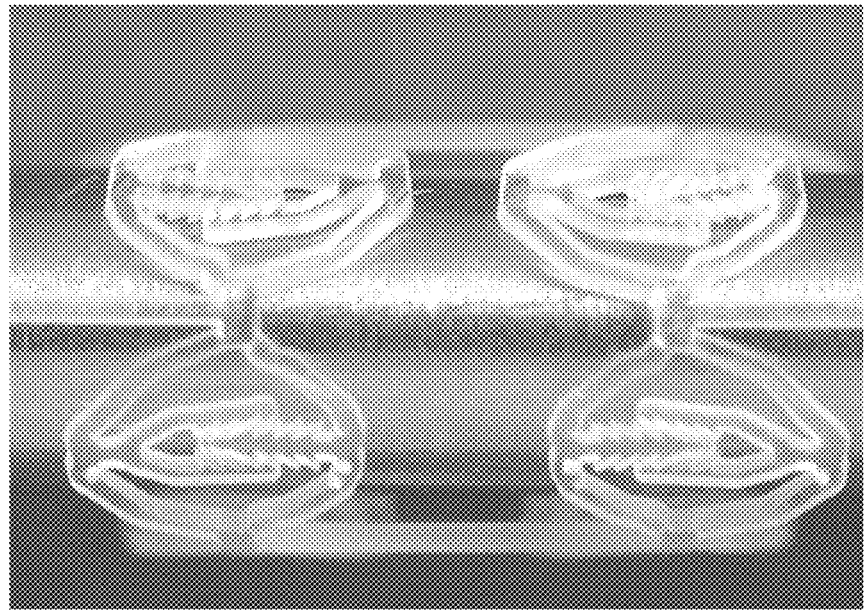
FIG. 18 depicts a stent sample deployed at 4 atmospheres.
Figure 19:
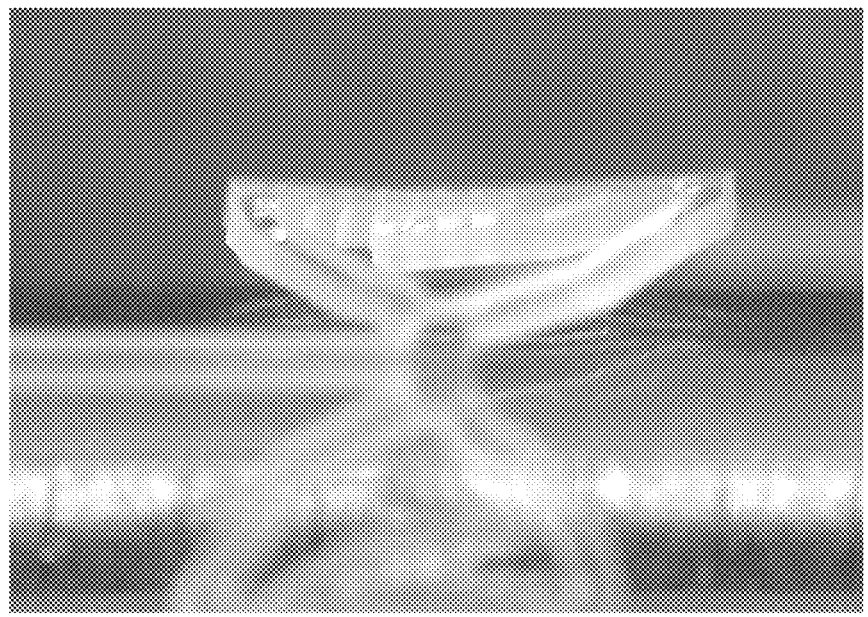
FIG. 19 is another view of the stent of FIG. 18.

FIG. 18 depicts the 2.75 mm sample deployed at 4 atmospheres. As shown in FIG. 18, the locking elements are beginning to engage. FIG. 19 is another view of the 2.75 mm sample which shows the bar arms of the cell have partially come out of the cylindrical plane of the catheter.

Figure 20:
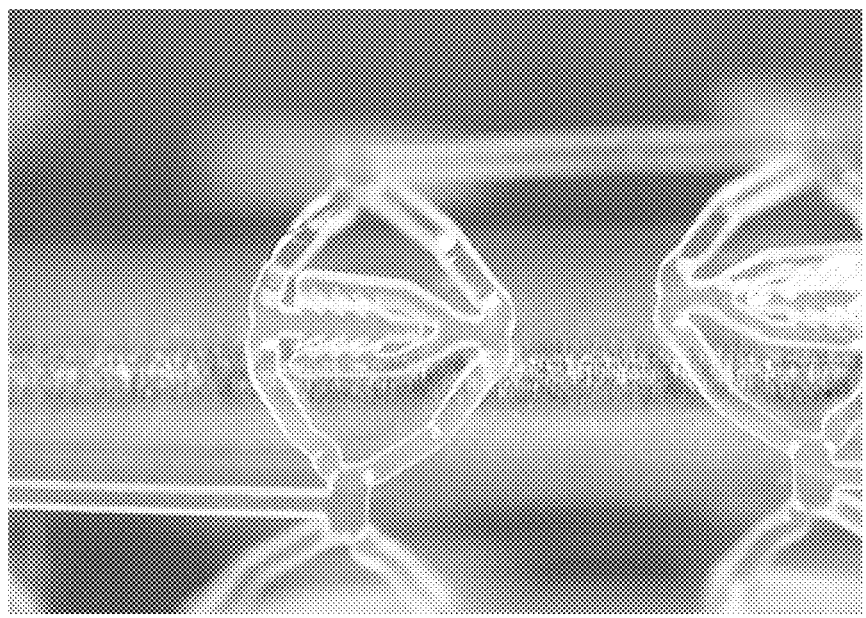
FIG. 20 depicts a stent sample deployed at 6 atmospheres.
Figure 21:
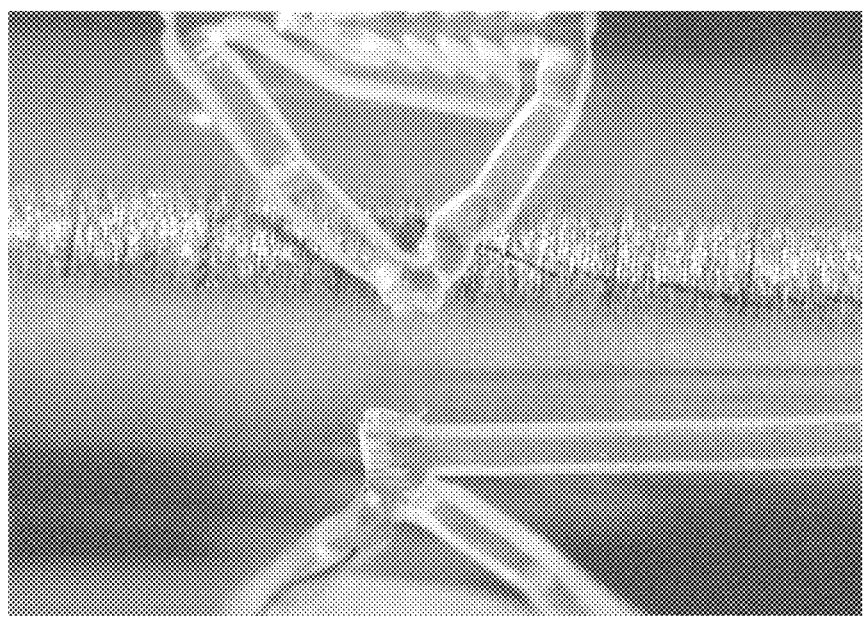
FIG. 21 is another view of the stent of FIG. 20 showing a fracture site.

FIG. 20 depicts an optical micrograph of the 3.5 mm sample deployed at 6 atmospheres. FIG. 20 shows that the locking mechanism is fully engaged. FIG. 21 is another view of the 3.5 mm sample which shows a fracture site at a circumferential link.

While particular embodiments of the present invention have been shown and described, it will be obvious to those skilled in the art that changes and modifications can be made without departing from this invention in its broader aspects. Therefore, the appended claims are to encompass within their scope all such changes and modifications as fall within the true spirit and scope of this invention.

What is claimed is:

1. A radially expandable intravascular stent, comprising:
a plurality of undulating interconnected bar arms comprising crests formed by the bar arms, at least one of the crests being a lockable crest, the lockable crest including:
a male locking element fixedly attached on one side of the lockable crest and a female locking element fixedly attached on another side of the lockable crest, wherein the male and female locking elements have an unlocked position and at least one locked position, the male locking element includes an engagement feature, the female locking element includes an engagement feature,
wherein in the unlocked position, the engagement feature of the male locking element is not engaged with the engagement feature of the female locking element,
wherein as the stent expands and the bar arms that form the lockable crest bend outward, the male and female locking elements move toward one another from the unlocked position to the at least one locked position in which the engagement feature of the male locking element engages the engagement feature of the female locking element, wherein the locked position inhibits or prevents a reduction in diameter of a ring formed by the bar arms
wherein the engagement feature of the male locking element is a plurality of teeth, and the engagement feature of the female locking element is a plurality of teeth.

2. The stent of claim 1, wherein the stent comprises a biostable and/or a biodegradable polymer.

3. The stent of claim 1, wherein the male locking element comprises a curved post and the female locking element comprises a slot.

4. The stent of claim 1, wherein the locked male and female locking elements inhibit expansion of the stent beyond a locked radius.

5. The stent of claim 1, wherein the male and female locking elements have a plurality of locked positions that enable the ring to be locked at more than one diameter.

6. The stent of claim 1, wherein when the stent expands and the bar arms that form the lockable crest bend outward, the teeth of the male locking element move across the teeth of the female locking element.

7. The stent of claim 1, wherein the male locking element and the female locking element are fixedly attached to the ring.

8. The stent of claim 7, wherein there is a second lockable crest among the crests formed by the bar arms, and the second lockable crest comprises:
   a second male locking element fixedly attached on one side of the second lockable crest and a second female locking element fixedly attached on another side of the second lockable crest, wherein the second male and female locking elements have an unlocked position and at least one locked position, the second male locking element includes an engagement feature being a lip or at least one tooth, the second female locking element includes an engagement feature being a notch or at least one tooth,
   wherein in the unlocked position, the engagement feature of the second male locking element is not engaged with the engagement feature of the second female locking element,
   wherein as the stent expands and the bar arms that form the second lockable crest bend outward, the second male and female locking elements move toward one another from the unlocked position to the at least one locked position in which the engagement feature of the second male locking element engages the engagement feature of the second female locking element, wherein the locked position inhibits or prevents a reduction in diameter of a second ring formed by the bar arms.

9. The stent of claim 8, wherein the second male locking element and the second female locking element are fixedly attached to the second ring.

10. A radially expandable intravascular stent, comprising:
    a plurality of undulating interconnected bar arms comprising crests formed by the bar arms, at least one of the crests being a lockable crest, the lockable crest including:
    a male locking element fixedly attached on one side of the lockable crest and a female locking element fixedly attached on another side of the lockable crest, wherein the male and female locking elements have an unlocked position and at least one locked position, the male locking element includes an engagement feature being a lip or at least one tooth, the female locking element includes an engagement feature being a notch or at least one tooth,
    wherein in the unlocked position, the engagement feature of the male locking element is not engaged with the engagement feature of the female locking element,
    wherein as the stent expands and the bar arms that form the lockable crest bend outward, the male and female locking elements move toward one another from the unlocked position to the at least one locked position in which the engagement feature of the male locking element engages the engagement feature of the female locking element, wherein the locked position inhibits or prevents a reduction in diameter of a ring formed by the bar arms,
    wherein the male and the female locking elements each include a first locking surface and a second locking surface, and when in the locked position, the first locking surface of the male locking element engages the first locking surface of the female locking element and the second locking surface of the male locking element engages the second locking surface of the female locking element.

11. The stent of claim 10, wherein:
    the engagement feature of the male locking element is a plurality of teeth on at least one of the locking surfaces of the male locking element, and the engagement feature of the female locking element is a plurality of teeth on at least one the of locking surfaces of the female locking element;
    when in the unlocked position, the teeth of the male locking element are not engaged with the teeth of the female locking element; and
    when the male and female locking elements move toward one another, the teeth of the male locking element engage with the teeth of the female locking element.

12. The stent of claim 11, wherein the male locking element comprises a curved post, the female locking element comprises a slot, the curved post includes a first curved side that carries at least some of the teeth of the male locking element, and the slot includes a first curved side that carries at least some of the teeth of the female locking element.

13. The stent of claim 12, wherein the curved post includes a second curved side that carries some of the teeth of the male locking element, and the slot includes a second side that carries some of the teeth of the female locking element.

14. The stent of claim 13, wherein in the locked position, the teeth on the first curved side of the post engages the teeth of the first curved side of the slot, and the teeth on the second curved side of the post engages the teeth of the second side of the slot.

15. The stent of claim 10, wherein the male locking element and the female locking element are fixedly attached to the ring.

16. The stent of claim 15, wherein there is a second lockable crest among the crests formed by the bar arms, and the second lockable crest comprises:
    a second male locking element fixedly attached on one side of the second lockable crest and a second female locking element fixedly attached on another side of the second lockable crest, wherein the second male and female locking elements have an unlocked position and at least one locked position, the second male locking element includes an engagement feature being a lip or at least one tooth, the second female locking element includes an engagement feature being a notch or at least one tooth,
    wherein in the unlocked position, the engagement feature of the second male locking element is not engaged with the engagement feature of the second female locking element,
    wherein as the stent expands and the bar arms that form the second lockable crest bend outward, the second male and female locking elements move toward one another from the unlocked position to the at least one locked position in which the engagement feature of the second male locking element engages the engagement feature of the second female locking element, wherein the locked position inhibits or prevents a reduction in diameter of a second ring formed by the bar arms.

17. The stent of claim 16, wherein the second male locking element and the second female locking element are fixedly attached to the second ring.

* * * * *